United States Patent
Garberoglio

(12) 
(10) Patent No.: US 6,400,987 B1
(45) Date of Patent: Jun. 4, 2002

(54) ACTIVE IMPLANTABLE DEVICE

(75) Inventor: Bruno Garberoglio, Turin (IT)

(73) Assignee: Sorin Biomedica Cardio S.p.A., Saluggia (IT)

( * ) Notice: Subject to any disclaimer, the term of this patent is extended or adjusted under 35 U.S.C. 154(b) by 0 days.

(21) Appl. No.: 09/115,317

(22) Filed: Jul. 14, 1998

(30) Foreign Application Priority Data

Aug. 13, 1997 (IT) ......................................... TO97A0744

(51) Int. Cl.[7] .............................................. A61N 1/365
(52) U.S. Cl. ....................................................... 607/18
(58) Field of Search ............................... 607/32, 60, 18

(56) References Cited

U.S. PATENT DOCUMENTS

| 5,496,351 | A | | 3/1996 | Plicchi et al. |
| 5,540,727 | A | * | 7/1996 | Tockman et al. ............. 607/18 |
| 5,626,630 | A | * | 5/1997 | Markowitz et al. ........... 607/60 |
| 5,752,976 | A | * | 5/1998 | Duffin et al. .................. 607/32 |

* cited by examiner

*Primary Examiner*—George R. Evanisko
(74) *Attorney, Agent, or Firm*—Popovich & Wiles, PA

(57) ABSTRACT

An active implantable device having a sensor capable of detecting signals indicative of the conditions of the wearer of the device; a processor capable of selectively identifying, from signals detected by the sensor, particular conditions of the wearer of the device such as to require urgent assistance, an actuator capable of inducing the performance of therapeutic actions on the body of the wearer upon the occurrence of the particular conditions of the wearer of the device and a telemetry system capable of signaling from the body of the wearer of the device the occurrence of the particular conditions of the wearer of the device.

3 Claims, 3 Drawing Sheets

ACTIVE IMPLANTABLE DEVICE

FIELD OF THE INVENTION

The present invention relates to implantable devices (or implants) of active type.

BACKGROUND OF THE INVENTION

This term "implants" is intended to indicate devices intended to be implanted in the body of a patient and the function of which is not limited to the replacement or functional assistance of an organ or a part of an organ of the human body (which may be the case, for example, with a cardiac valve prosthesis or so-called vascular graft). On the contrary, an active implantable device is generally able to recognise the occurrence of a particular physiological picture and then give a specific reaction.

Cardiostimulators (currently known as pacemakers) are a typical example of active implantable devices: these latter are in general able to recognise the absence or insufficiency of the natural cardiac stimulation and to respond in such a way as to replace this missing or insufficient stimulation with a stimulation produced by the device itself, acting as a function of the activity of the patient (so-called "rate responsive" stimulators).

It is also known that implant devices such as cardiostimulators as mentioned above, can be provided with a so-called telemetry function which, as well as allowing programming of the stimulator from a distance (and therefore in an extracorporeal manner), also makes it possible to emit, for example to a monitoring station supervised by an operator, signals indicative of the conditions of the wearer.

Also known in the art are so-called "drug dispenser" implants which are able to achieve a targeted delivery of a predetermined drug, also in dependence on a signal indicative of the establishment of particular conditions in the body of the patient.

The present invention, which has been developed with a view to preferential (although not exclusive) application to the treatment of cardiac conditions, is based on the recognition of several essential facts:

almost all active implants available up to now are only able to treat cardiac conditions of the "electrical" type, such as for example insufficient stimulation;

some electrical cardiac conditions (such as for example, atrial fibrillation) are not treatable in a satisfactory manner with only electrical stimulation, whilst, on the other hand, important results in the treatment of such conditions have been obtained with a pharmaceutical treatment; and important cardiac conditions (such as the so-called congestive heart failure, currently called CHF) are difficult to monitor, expensive to treat and often have unfavourable consequences if not monitored and treated in a timely manner.

By examining more closely the two above-considered conditions (which it is intended should not exhaust the range of possible applications of the invention) the following can be observed.

Atrial fibrillation is essentially a form of cardiac arrhythmia characterised by rapid and irregular atrial electrical impulses and by inefficient atrial contractions. The atrial rhythm can be up to 400–650 beats per minute, whilst the ventricular rhythm varies in an irregular manner between 100 and 180 beats per minute. Atrial fibrillation can have a paroxysmic origin at different points of the sinoatrial node and is typically multifocal. It may terminate spontaneously in an unexpected manner, but often becomes chronic.

The consequences lead substantially to a loss of effectiveness of the atrial contraction (the so-called "atrial kick") and to a loss of the correct management of the cardiac frequency according to metabolic requirements (so-called chronotropic incompetence), and to the frequent manifestation of arrhythmias with an irregular and rapid ventricular rhythm. All this leads to a general reduction of efficiency in the pumping action of the cardiac muscle (unbalanced, low resistance to forces), to an increase in the formation of intracardiac thromboses (with consequent risk of cerebral ictus), to ventricular tachycardia, and, in general, to a reduced quality of life with increasing risk of mortality.

The main methods of treatment currently known range from surgical treatment (which is traumatic and certainly not suitable in all cases) to external electric defibrillation (which at times is not effective and may not be in time) to ablation of the ectopic sites at the base of the arrhythmias (a technique which must, however, remain of an experimental nature), to pharmacological treatment. This latter type of treatment, which is of an anti-rhythmic nature, is essentially directed at reducing the recurrence of fibrillation (by administration of quinidine, flecainide, propafenone, sotalol or disopyramide), reducing the cardiac frequency (by the administration of digitalis products and b-blockers) or has an anti-coagulant function to reduce the risk of ictus and other thromboembolic events (administration of aspirin, warfarin), and is certainly promising, but is not conclusive in that it is not free from contra-indications or risks.

It is possible therefore to assert that in order to be certainly effective of treatment must to some extent be able to count at least in principle, on at least some of the forms of treatment described above, performed in a co-ordinated framework of concurrent actions of diverse nature.

This is also substantially true for congestive heart failure (CHF). This latter essentially leads to a weakening and then a reduced function of the cardiac muscle as a pumping member, and is in particular able to cause significant difficulty in filling and/or emptying of the left ventricle and therefore an insufficient cardiac capacity.

The main consequences are dispnea and a greater sense of fatigue from effort, ventricular arrhythmia (and in particular atrial fibrillation), an increase in sympathetic tone with a reduction of parasympathetic tone, thromboembolisms, retention of fluids and an increased risk of myocardiac infarction. All this with a significant increase in the mortality rate in particular by unexpected death and by terminal cardiac insufficiency.

The current methods of treatment are pharmacological, with the administration of digitalis products, diuretics or vasodilators. Such treatment, which is not always effective and the therapeutic effect of which is not demonstrated, can be the herald of collateral effects.

Electrical stimulation has also been practised, which however is of limited effectiveness and is only usable in a small category of patients, the same considerations applying to the technique of cardiomyoplasty.

A greater effectiveness, at least in some cases and on a temporary basis, can be achieved by recourse to ventricular assistance devices (VAD) or to artificial hearts. This, however, involves, as is well known, arrangements which are usable for only a limited time, and are such as to require intensive hospital assistance (with consequent high treatment costs), involving intrinsically more difficult techniques allied to the fact that ventricular assistance devices usually require, for their operation, service supply means (electrical energy, fluid under pressure etc.) from sources located outside the body of the patient, via supply lines of a transcutaneous nature.

A limited solution is represented by (total or partial) transplant of the cardiac muscle, a solution which however comes up against limited availability of donors, problems of biocompatability, high initial and follow up costs and risks of possible degeneration.

The experience of treating these conditions demonstrates that very often the possibility of achieving an effective treatment, whatever its type, depends critically on the possibility of monitoring the patient's condition and/or signalling in a timely manner to the outside (to the patient himself and/or to an assistance centre to which he can go) the establishment of or, better still, the probable approach of a crisis state. In this way it is possible, for example, to cause the patient to interrupt an activity which may be critical because of the conditions and/or to go straight to an assistance centre, or even cause the assistance centre, alerted in an automatic manner, to locate the patient, leading it to him, to then subject him to the specific treatments such as those which can be performed, for example, in an intensive care unit of a hospital.

SUMMARY OF THE INVENTION

The present invention seeks to provide an active implant device able to respond in an optimal manner to the detection and treatment requirements described above. According to the present invention, this object is achieved by an implant device having the characteristics specifically set out in the claims.

This invention is an active implantable device comprising a sensor means capable of detecting signals indicative of the conditions of the wearer of the device; a processor means capable of selectively identifying, from signals detected by the sensor means, particular conditions of the wearer of the device such as to require the intervention of assistance; an actuator means capable of inducing the performance of therapeutic actions on the body of the wearer upon the occurrence of the particular conditions of the wearer of the device; and a telemetry means capable of signalling out from the body of the wearer of the device the occurrence of the particular conditions of the wearer of the device. The sensor means may include an interface unit capable of transferring to the processor means the signals detected by at least one sensor element implanted in the body of the patient. Preferably, the sensor means is sensitive to one of the following: electrocardiograph signals (ECG) of the wearer of the device; the signal relating to the natural heart acceleration (NHA) of the wearer of the device, and the blood pressure (BP) of the wearer of the device.

The device may also comprise at least one interface for converting respective control signals generated by the processor means into respective activation signals for at least one of the actuator means for performing a therapeutic action on the body of the wearer of the device.

Preferably, the actuator means is capable of inducing at least one of the following therapeutic actions on the body of the wearer of the device: an electrical stimulation action, and a drug infusion.

The telemetry means may comprise a short distance telemetry section for the transmission, from the body of the wearer of the device, of monitoring signals identifying the particular conditions of the wearer of the device identified by the processor means from signals detected by the sensor means.

Alternatively, the telemetry means may include a long distance telemetry section for the transmission, from the body of the wearer of the device, of at least one warning signal identifying the occurrence of the particular conditions of the wearer of the device identified by the processor means from the signals detected by the sensor means.

The telemetry means may have at least one of the following associated units: a telecommunications unit for sending warning and/or data signals to a telecommunications network, and a position location unit for locating the whereabouts of the wearer of the device. The telecommunications unit may be in the form of a mobile radio unit.

The position locating unit preferably is a position locating unit of a telecommunications network. The position locating unit is capable of sending the associated position locating signal of the wearer of the device to the telecommunications unit for forwarding a corresponding message for locating the position of the wearer of the device.

BRIEF DESCRIPTION OF THE DRAWINGS

The invention will now be described, purely by way of non-limiting example, with reference to the attached drawings, in which.

DETAILED DESCRIPTION OF THE PREFERRED EMBODIMENTS

Figure 1:
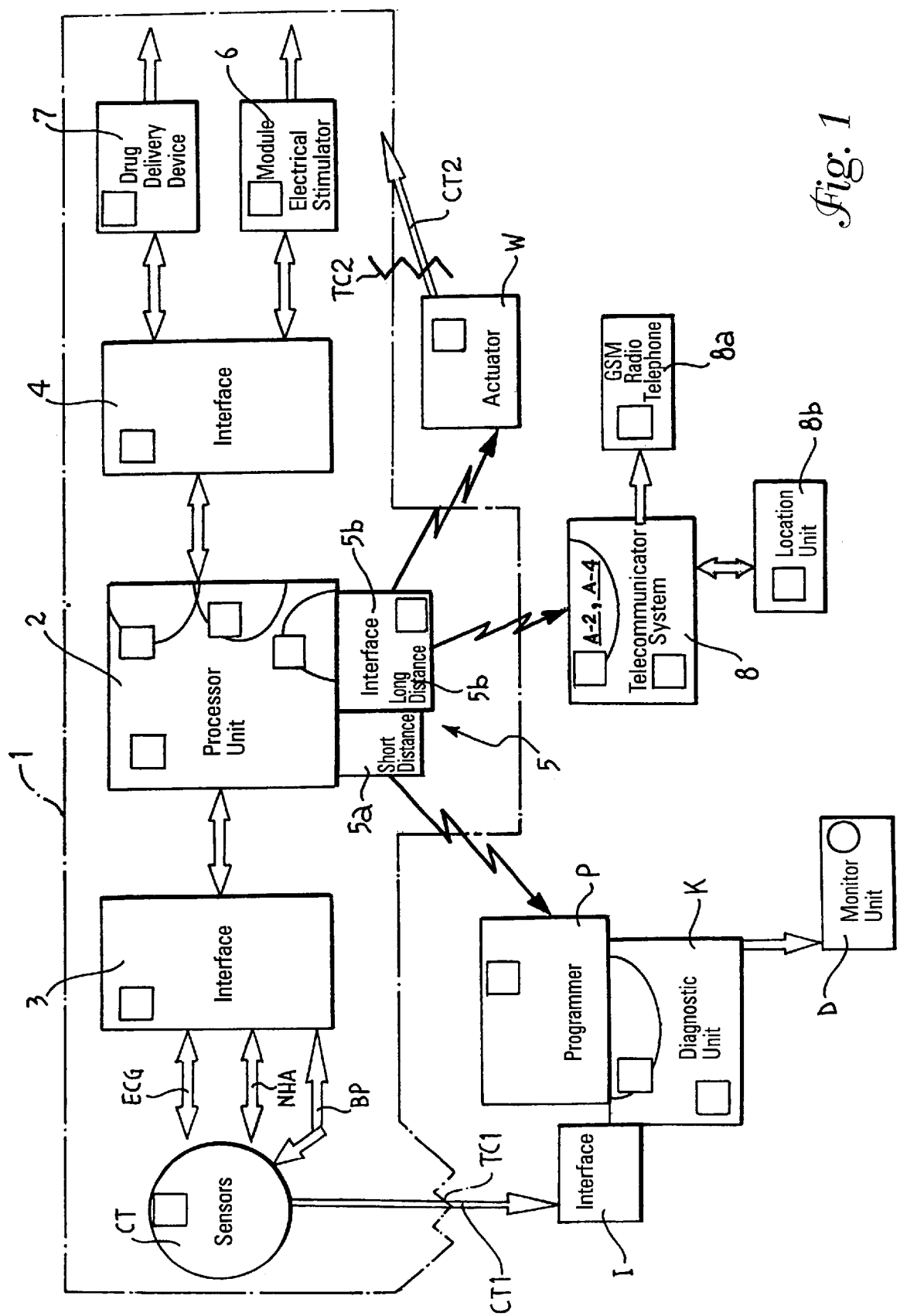
FIG. 1 illustrates, in block schematic form, the general architecture of an active implantable device according to the invention.

In the block diagram of FIG. 1, the implant device according to the invention is generally indicated 1.

The core of the device is constituted by a processor unit or CPU which may essentially be constituted by a microprocessor.

Three modules 3, 4 and 5 lead to the processor unit 2 the functions of which modules will be described in more detail hereinafter but which, as far as their nature is concerned, are essentially configurable as interfaces.

One or more sensor means (collectively indicated CT) is or are connected to the interface 3 which sensors, with the device 1 implanted in the body of a patient, detect signals indicative of the patient's condition, mainly as far as the manifestation—or possible manifestation—of syndromes linked to conditions such as for example the cardiac conditions described in the introductory part of the present description.

By way of example, this can involve (emphasising that the list provided here is of purely exemplary nature in that the specific possibilities for realisation are practically infinite):

a first sensor means which detects a signal or several signals relating to the patient's electrocardiogram (ECG), second sensor means which detect the blood pressure (BP) of the patient, and/or third sensor means which detect the so-called natural heart acceleration (NHA).

For a detailed description of the operational criteria and realisation of a sensor of this nature, reference can usefully be had to the U.S. Pat. No. 5,496,351.

From the physical point of view the sensor means ECG, BP, NHA can be configured in a different manner (widely known second morphology). For the most part these sensors are essentially configurable as respective catheters or parts of respective catheters which branch out from the body of the device 1 (in a manner which will be better illustrated hereinafter with reference to FIGS. 2 and 3) towards the corporeal sites where they detect the parameters.

Naturally, the device 1 according to the invention can also be configured in such a way that the signals from one or more of the catheters CT, possibly also from a catheter or sensor CT1 of different type, are sent directly out through a transcutaneous passage TC1 in view of the processing according to criteria which will be illustrated better hereinafter.

Starting from the signals obtained through the interface 3, the processor unit 2 is able to develop (according to known criteria on the stock of processing algorithms and programming data available within it or in members such as memories associated with it) one or more functions which can be substantially reduced to four fundamental functions:

identification of a framework of conditions of the patient corresponding to a risk situation occurring and/or close to arising;

identification of respective modes of therapeutic intervention (intended to be performed according to criteria which will be illustrated better hereinafter);

identification of a diagnostic framework for the risk situation previously identified; and definition and performance of the intervention actions (which will be better illustrated hereinafter) which characterise the device 1 as a device of active type.

The function of the interface 4 is essentially to translate the therapeutic indications and the action indications developed within the processor unit 2 into corresponding interventions on the body of the patient.

These interventions can be, for example:

electrical stimulation performed, in a known way, by a module or unit 6 substantially equivalent to an electric cardiostimulator (so-called pacemaker or implantable defibrillator);

interventions of pharmacological type effected, for example, with one or more drug delivery device 7 of the type currently called "drug dispensers"; and interventions of combined type, directed to exploiting the possible synergistic effect of the electrical actions and the administration of drugs so as possibly to limit the absolute levels and the unwanted effects of both interventions. Both the type of electrical stimulator device or devices 6 and the type of drug delivery device or devices 7 correspond to prior art types known per se. This therefore makes a detailed description of the associated characteristics thereof superfluous in this document. Although, for simplicity of illustration, the implant device indicated 1 has been shown in FIG. 1 as including (see the broken line) the sensor devices (catheters) indicated collectively CT, as well as the "actuator" devices 6 and 7, it is to be remembered that the illustration of FIG. 1 is only one of the various possible embodiments of the invention.

Figure 2:
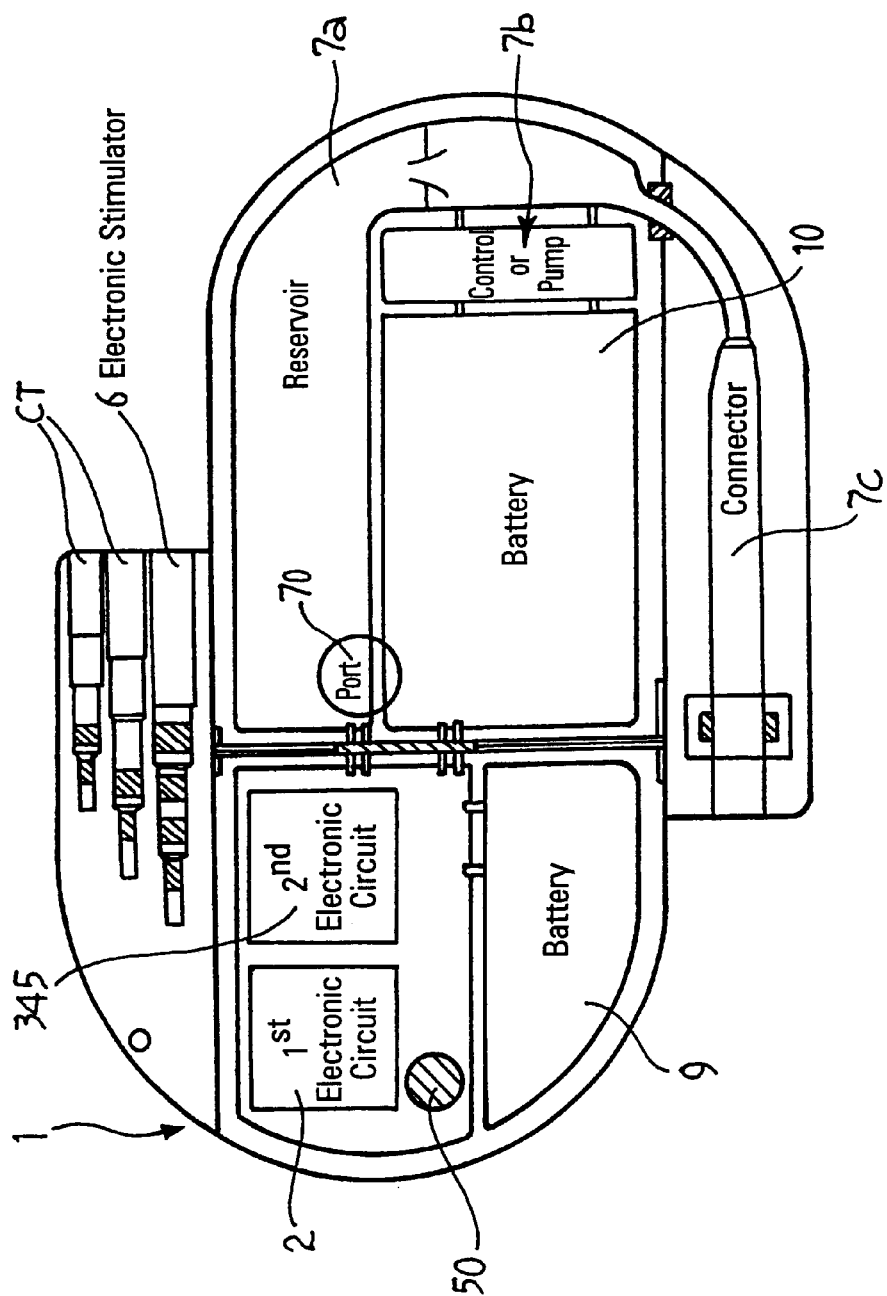
FIG. 2 illustrates a first possible embodiment of a device according to the invention.
Figure 3:
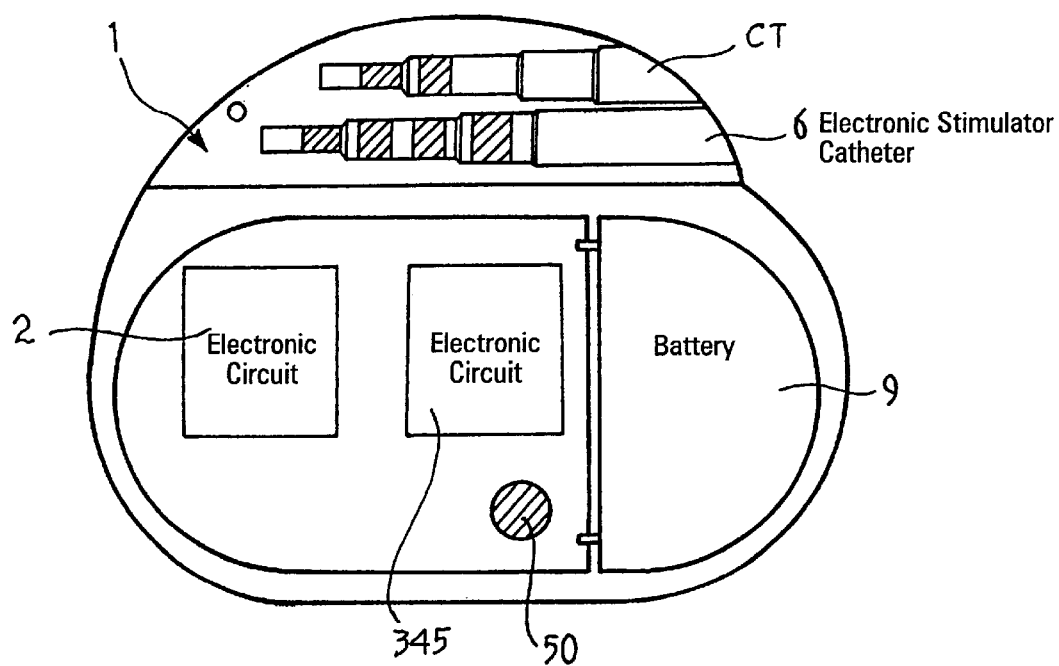
FIG. 3 illustrates a simplified embodiment of a device according to the invention.

In this respect it is in fact possible to go from minimal embodiments of the device 1, such as that illustrated in FIG. 3, where in fact the device 1 itself only comprises the associated processor part (the unit 2 and the interfaces 3 and 5) with provision of connectors for connection to the sensors CT and/or the actuators 6, 7, to so-to-speak intermediate embodiments (which are the most frequent), of the type illustrated in FIG. 2, where the device includes, as well as the processor part, a 20 connector assembly for connection of the sensors CT, incorporating within it the stimulator device 6 and/or part (for example the externally rechargeable reservoir) of the infuser device 7. It is possible then, to arrive, at least in some particular cases, at situations of greater integration in which the device 1 also incorporates within its interior one or more sensors, possibly in combination with one or more sensors CT.

The interface 5 is essentially dedicated to the "telemetry" functions that is to say the exchange of signals (typically in the form of radio signals although signals of alternative, different type are possible, such as magnetic or ultrasonic signals) to and from the external environment.

The specific constructional details of one such interface unit (and in particular the configuration of respective transmitter and/or receiver apparatus) correspond to arrangements known per se in the art, which therefore do not require to be illustrated in detail here.

In the preferred exemplary embodiment of FIG. 1 the interface 5 can be seen as ideally subdivided into two sections respectively indicated 5a and 5b.

The section 5a is essentially dedicated to short distance telemetry functions (the associated transmission members having a range of the order of several centimetres or tens of centimetres). The interface 5a allows, for example, the (unidirectional, but preferably bidirectional) connection with a programming device P able to receive and process signals processed in the unit 2 relating to the "analysis" of the patient's situation in view of the processing of diagnostic indications performed, for example, in a unit K provided for this purpose, preferably in view of the display on a monitoring unit D. This is all in the typical framework of assistance brought to the patient wearing the device 1 when in "hospitalisation" conditions (including in this term all situations in which the patient is assisted by third parties, typically medical or paramedic personnel at a hospital site, outpatient ward or at least in the ambit of an assistance unit such as an ambulance or, more simply, at home). A programmer P and/or the diagnostic unit K may possibly receive signals from sensors such as the transcutaneous catheter indicated CT1 via an associated interface indicated I.

Thus, as indicated in the introductory part of the specification, the system according to the invention is based on the recognition of the relevance, for the purposes of obtaining effective treatments, of being able to arrange that the patient can be taken to hospitalisation conditions (in the wider meaning of this term as described above) as rapidly as possible and/or to develop as soon as possible the most suitable therapeutic interventions so that the patient can receive the necessary care before a decided aggravation of his clinical condition intervenes.

The actuator devices 6 and 7 described above operate in this latter direction with the further possibility offered by the interface 5 (and for example by the section 5b which constitutes the so-called long distance telemetry section: although the same function could also be performed by the short distance telemetry section 5a) of allowing the activation of further actuators not implanted in the utiliser's body. This relates, for example, to another device W for infusion of drugs, worn by the wearer and capable of selectively introducing a drug into the body of the wearer. This can take place, for example, by means of a further catheter CT2 which extends through a further transcutaneous passage CT2 (which may possibly coincide with the transcutaneous passage TC1 with the further possibility of unifying the catheters CT1 and CT2 in a single catheter).

Naturally, the actuator indicated W could be of different kind, other than a drug infuser: it could be an electric or even mechanical stimulator device. The actuator or actuators W (in fact there could be more than one of them) chosen for extracorporeal location, and therefore not an implant, may assume this configuration for different reasons. For example, because their dimensions and their particular mode of operation prevent their location as an implant, or more simply, because their use may be envisaged for a limited time interval, for example until an acute phase of a determined condition is over. Furthermore, the action of the actuator or actuators W may be demanded as much in a direct manner at the interface 5 in an automatic way as to provide an intervention of the patient wearing the device. In this case (not specifically illustrated in the drawings) the interface 5 produces—upon identification of a particular framework of conditions in the patient—a warning signal (acoustic and/or sound but also of different nature) with the consequent request, expressed to the patient, to act on the actuator or actuators W to produce a therapeutic intervention. Naturally the solution which provides automatic control of the actuator or actuators W by the unit 2 is preferable for all those interventions in which it must be presumed that a possible warning signal directed to the wearer may not be perceived thereby and/or not converted into an effective intervention.

The main function of the remote telemetry section 5b (by remote telemetry is meant a telemetry action able to have a range of the order of a meter or more) is that of producing (upon occurrence, actual or foreseen, of a framework of conditions of the patient such as to require an assistance intervention) the activation of a true and proper telecommunications system 8 for the purpose of allowing the location of the patient with a view to allowing him to receive the required assistance.

Such telecommunications systems may be configured as an alternative form or may be integrated as a telephony system, for example of the GSM radio telephone type with a respective unit 8a which, upon determination of a critical state in the patient, recognised as such in the unit 2, puts out a call (for example a telephone call) to an assistance post with the emission of a message which signals the fact that the wearer of the device 1 probably requires interventive assistance, with the possible addition of signals which convey data relating to the state of the wearer: this is achieved in such a way as possibly to allow the assistance post to evaluate the level of seriousness of the state of the wearer.

In addition, or alternatively, the system 8 may include a locating unit, for example of the satellite radio locating type called GPS (the use of which is widely diffused, for example, on leisure vessels and on various vehicles including aircraft, in particular the so-called ultralights or ULM) or may be included in a local telecommunications network (DECT) able to detect the exact position of the wearer by providing a corresponding signal to the system 8, usually with a view to forwarding the corresponding signal to persons who must perform the intervention on the wearer.

The telecommunications system 8 (including the units 8a and 8b) lend themselves at least in theory to being integrated at least in part into the implant device 1.

The diagram of FIG. 1 makes reference, by way of example, to an alternative solution, in which the system 8 is external of the device 1 and therefore in general is worn by the wearer, but not implanted therein, communicating with the unit 2 through the telemetry interface 5.

This solution is preferential in that the function represented by the unit 8a can easily be integrated, for example, in a mobile telephone carried by the patient, the same also being true as far as the location unit 8b is concerned.

The diagram of FIG. 2 illustrates, in dimensions corresponding approximately to the real dimensions, the possibility of forming the device 1 in the form of an implantable casing within the interior of which are housed:

a first electronic circuit such as a microprocessor which combines the functions of the processor unit 2;

a further electronic circuit, also in this case another microprocessor, for example, which combines the functions of the interfaces 3, 4 and 5—or a good part of these—and for this reason has been identified in FIG. 2 with the reference 345;

a first supply source constituted for example by a battery 9 (of the type currently utilised for implant devices such as pacemakers) which provides primary supply to the electronic circuits 2 and 345, and the associated antenna unit 50 capable of possibly serving both the short distance telemetry section 5a and the long distance telemetry distance 5b;

at least part of an infuser device such as the device 7 and in any event a reservoir 7a for a drug with an associated infusion system with associated control 7b (for example having a pump) and a connector 7c for connection to an infusion catheter: or with the possible provision of a port 70 for transcutaneous recharging of the reservoir 7a by means of a syringe;

a further battery 10 capable of supplying, for example the pump 7b of the infusion system and any other actuator having characteristics of high electrical energy consumption, such as for example an electrical stimulator device, such as the electric stimulator device 6 when this is directly incorporated in the device 1 (this solution not explicitly illustrated in FIG. 2);

a plurality of further connectors for the connection of catheters, these being one or more catheters having a sensing function (such as the catheters CT), or one or more catheters with an actuator function such as for example a stimulation catheter which incorporates the function of the device 6 for example by transferring stimulation control signals from the device I to the stimulator device itself, implanted in the body of the user.

FIG. 3 on the other hand makes reference to a further possible embodiment of a device according to the invention, of simpler and more elementary type: the references used in FIG. 3 illustrate the same or at least functionally equivalent parts to those indicated with the same references in FIG. 2. In the device 1 of FIG. 3 there are therefore present two electronic circuits 2 and 345, the latter having an associated antenna 50, both supplied by a battery 9. All with the provision, in the casing of the device 1, of connectors for the connection of at least one catheter CT with a sensor function and a catheter with an actuator function such as, for example, an electric stimulation catheter 6.

As already described above, the embodiments of FIGS. 2 and 3 must be considered purely exemplary in that, the principle of the invention remaining the same, the details of construction and the embodiments can be widely varied with respect to what is described and illustrated, without by this departing from the ambit of the present invention. This is true, in particular, as far as the actuation by the processor means (for example the unit 2) is concerned, the therapeutic actions (here exemplified by the actuators 6 and 7) and remote alarm signals (telemetry interface 5 and in particular the section 5b ). It is not, in fact obligatory that the two functions be always performed in parallel.

The unit 2 may in fact be configured in a manner known per se such as to be able to follow, according to the particular framework of conditions of the patient identified from time to time, at least three different intervention strategies:

simple activation of the actuators (6 and/or 7, for example) with therapeutic intervention usually signalled to the outside (short distance telemetry section 5a, with monitoring function), but without activation of the "alarms" tied to the activation of the system 8;

therapeutic intervention, with activation of the alarms and;

activation of the alarms to the outside, without development of any therapeutic intervention.

Finally, it is again indicated that the device according to the invention is intended to intervene, upon occurrence of particular conditions of the wearer of the device, such term including—as explained several times above—both definitive occurrence (that is to say actually happening), and the foreseen and/or imminent occurrence of the conditions.

What is claimed is:

1. A system for providing treatment to the heart of a patient comprising:

a first sensor for sensing the patient's electrocardiograph and providing a first signal indicative thereof;

a second sensor for sensing the natural heart acceleration of the patient's heart and providing a second signal indicative thereof;

a third sensor for sensing a blood pressure of the patient and providing a third signal indicative thereof, the first, second, and third sensors being sized for implantation within the patient's body;

first and second therapy devices sized for implantation in the patient's body;

a third therapy device sized and configured to be attached externally to the patient's body;

a telemetry communicator sized for implantation in the patient's body; and a processor sized for implantation in the patient's body, the processor connected to receive the first, second and third signals, the processor being configured to identify based on the first, second and third signals a risk situation of the patient which requires therapeutic intervention, identification and selection of a specific therapeutic intervention appropriate for treatment of the risk situation and to generate and provide to the first and second therapy devices an activation signal based on the selected therapeutic intervention;

wherein the telemetry communicator is connected to receive and transmit the activation signal and wherein the third therapy device is configured to receive the activation signal from the telemetry communicator, and wherein the processor is further configured such that the activation signal results in implementation of the selected therapeutic intervention by activating the first therapy device only, by activating the second therapy device only, by activating both the first and second therapy devices, or by activating the third therapy device.

2. The system of claim 1 wherein the telemetry communicator is configured for short distance telemetry.

3. The system of claim 1 wherein the telemetry communicator is configured for long distance telemetry.

* * * * *